(12) United States Patent
Gould

(10) Patent No.: US 10,485,828 B1
(45) Date of Patent: Nov. 26, 2019

(54) NUTRITIONAL SUPPLEMENT

(71) Applicant: THYVITA HEALTH LTD. CO., Simpsonville, SC (US)

(72) Inventor: Rebecca A. Gould, Simpsonville, SC (US)

(73) Assignee: THYVITA HEALTH LTD. CO., Simpsonville, SC (US)

( * ) Notice: Subject to any disclaimer, the term of this patent is extended or adjusted under 35 U.S.C. 154(b) by 0 days.

(21) Appl. No.: 16/131,303

(22) Filed: Sep. 14, 2018

Related U.S. Application Data

(60) Provisional application No. 62/762,239, filed on Apr. 26, 2018, provisional application No. 62/606,220, filed on Sep. 14, 2017.

(51) Int. Cl.

| | | |
|---|---|---|
| *A61K 33/34* | (2006.01) |
| *A23L 33/165* | (2016.01) |
| *A23L 33/155* | (2016.01) |
| *A61K 31/07* | (2006.01) |
| *A61K 31/122* | (2006.01) |
| *A61K 31/197* | (2006.01) |
| *A61K 31/355* | (2006.01) |
| *A61K 31/375* | (2006.01) |
| *A61K 31/4188* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/593* | (2006.01) |
| *A61K 31/675* | (2006.01) |
| *A61K 31/714* | (2006.01) |
| *A61K 33/04* | (2006.01) |
| *A61K 33/06* | (2006.01) |
| *A61K 33/10* | (2006.01) |
| *A61K 33/18* | (2006.01) |
| *A61K 33/24* | (2019.01) |
| *A61K 33/26* | (2006.01) |
| *A61K 33/30* | (2006.01) |
| *A61K 33/32* | (2006.01) |

(52) U.S. Cl.
CPC ............ *A61K 33/34* (2013.01); *A23L 33/155* (2016.08); *A23L 33/165* (2016.08); *A61K 31/07* (2013.01); *A61K 31/122* (2013.01); *A61K 31/197* (2013.01); *A61K 31/355* (2013.01); *A61K 31/375* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/593* (2013.01); *A61K 31/675* (2013.01); *A61K 31/714* (2013.01); *A61K 33/04* (2013.01); *A61K 33/06* (2013.01); *A61K 33/10* (2013.01); *A61K 33/18* (2013.01); *A61K 33/24* (2013.01); *A61K 33/26* (2013.01); *A61K 33/30* (2013.01); *A61K 33/32* (2013.01); *A23V 2002/00* (2013.01)

(58) Field of Classification Search
CPC ...... A61K 33/34; A61K 31/07; A61K 31/122; A61K 31/197; A61K 31/355; A61K 31/375; A61K 31/4188; A61K 31/455; A61K 31/51; A61K 31/519; A61K 31/525; A61K 31/593; A61K 31/675; A61K 31/714; A61K 33/04; A61K 33/06; A61K 33/10; A61K 33/18; A61K 33/24; A61K 33/26; A61K 33/30; A61K 33/32; A23L 33/165; A23L 33/155; A23V 2002/00

See application file for complete search history.

(56) References Cited

U.S. PATENT DOCUMENTS

| | | | | |
|---|---|---|---|---|
| 2004/0001874 A1* | 1/2004 | Davidson | ............... | A23L 33/30 424/439 |
| 2009/0196862 A1* | 8/2009 | Davis | .................. | A61K 31/593 424/94.1 |
| 2009/0220619 A1* | 9/2009 | Cotter | .................. | A23L 33/105 424/638 |
| 2016/0129058 A1* | 5/2016 | Chang | ................. | A61K 35/747 424/93.3 |

\* cited by examiner

*Primary Examiner* — Doan T Phan

(74) *Attorney, Agent, or Firm* — J. Bennett Mullinax, LLC

(57) ABSTRACT

A nutritional supplement having a combination of minerals and chelated nutrients is provided that offers therapeutic benefits to individuals having thyroid regulation conditions. The formulation is also beneficial for other medical conditions associated with polar uptake of vitamins and nutrients within the digestive system of individuals, including, but not limited to individuals suffering from auto-immune diseases.

4 Claims, 1 Drawing Sheet

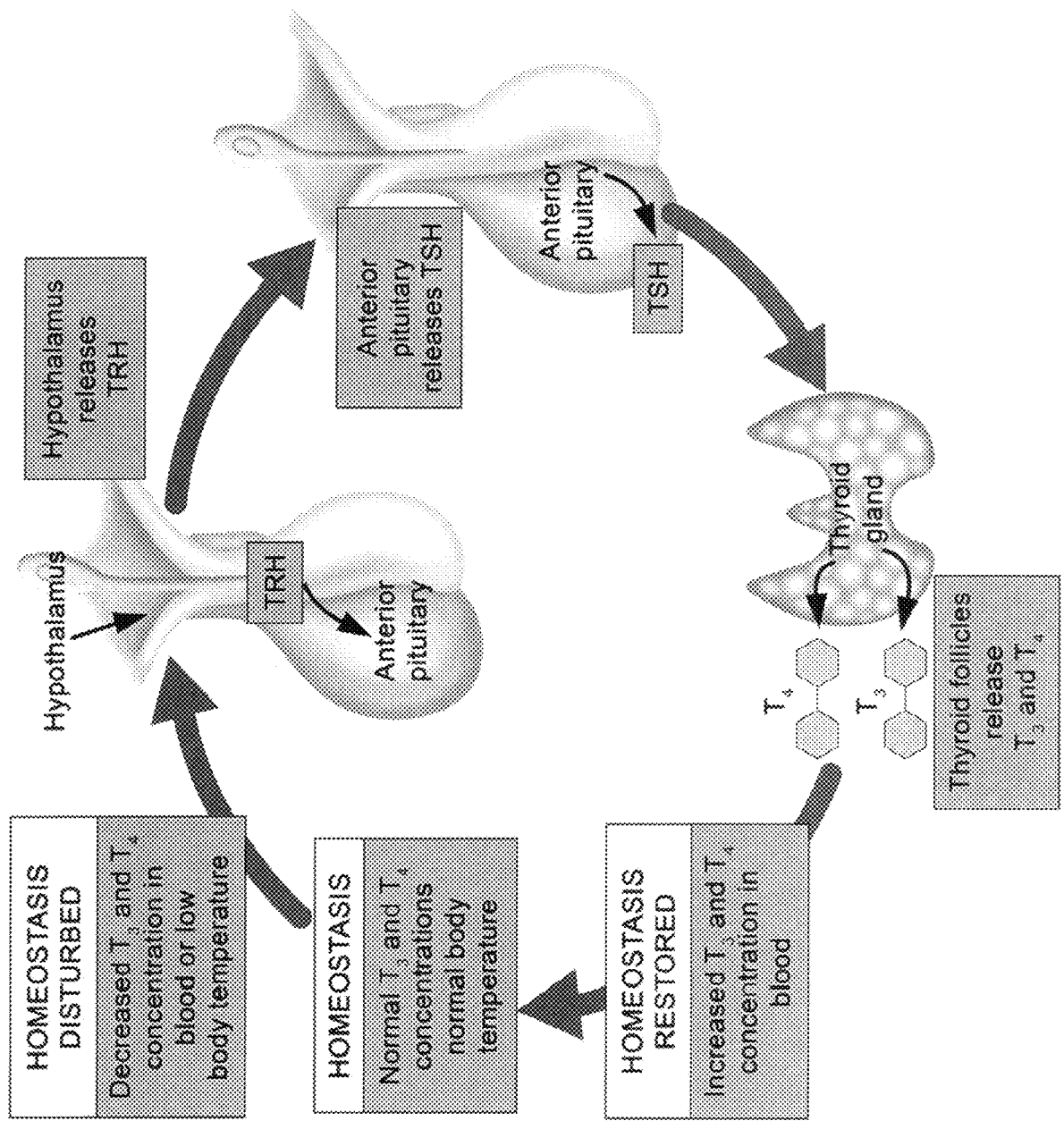

NUTRITIONAL SUPPLEMENT

RELATED APPLICATIONS

This application claims the benefit of U.S. Application Ser. No. 62/606,220 filed Sep. 14, 2017 and 62/762,239 filed on Apr. 26, 2018 and which are both incorporated herein by reference in their entirety.

FIELD OF THE INVENTION

This invention is directed towards a nutritional supplement that compensates for nutritional deficiencies which are often associated with hypothyroidism. In addition, this invention is directed to a nutritional supplement in the form of a tablet or capsule providing a formula that has enhanced absorption capabilities with individuals, including individuals with autoimmune or other nutritional deficiencies.

BACKGROUND OF THE INVENTION

This invention relates generally to nutritional supplements including supplements that include multi-vitamins along with various mineral supplements. While there are a wide number of various nutritional supplements that are known, there remains room for variation and improvement within the art.

SUMMARY OF THE INVENTION

It is one aspect of at least one of the present embodiments to provide a formula that provides a therapeutic dosing of a nutritional supplement that is more readily absorbed by an individual that comprises the following vitamins and nutrients in useful daily dosage ranges:
Vitamin A (beta carotene) 2500-3500 IU
Vitamin C (Ascorbic Acid) 250-700 mg
Vitamin D3 (Cholecalciferol) 3000-6000 IU
Vitamin E (d-alpha tocopherol) 15-30 IU
Vitamin K (phytonadione) 10-50 mcg
Vitamin B1 (thiamin HCl) 0.75-3.0 mg
Vitamin B2 (riboflavin) 1.0-2.5 mg
Niacin 10-40 mg
Vitamin B6 (pyridoxine HCl) 1-4 mg
Folic Acid 150-500 mcg
Vitamin B12 (methylcobalamin) 4-8 mcg
Biotin 250-1000 mcg
Pantothenic acid (Ca d-pantothenate) 2.5-20 mg
Calcium (Ca Carbonate) 200-1500 mg
Iron (ferrous fumarate) 10-30 mg
Iodine 75-300 mcg
Zinc (Zn Oxide) 7.5-35 mg
Magnesium (as Mg Citrate) 100-300 mg
*Selenium 7.5-30 mcg
*Copper 0.5-4.0 mg
*Manganese 0.5-4.0 mg
*Chromium (Chromium Nictonate Glycinate) 80-200 mcg
(*Albion® (Clearfield, Utah USA) brand amino acid chelated minerals are utilized as noted above)

It is a further aspect of at least one embodiment of the present invention to provide for a nutritional supplement that helps establish and maintain T3 and T4 ratios.

It is a further aspect of at least one embodiment of the present invention to provide for a nutritional supplement that promotes the human body's ability to convert T4 to T3.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

FIG. 1 is a diagram of a thyroid gland feedback loop.

DESCRIPTION OF THE PREFERRED EMBODIMENT

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5. As used herein, the term "above" refers to 5 percent plus or minus the stated amount In describing the various FIGURES herein, the same reference numbers are used throughout to describe the same material, apparatus, or process pathway. To avoid redundancy, detailed descriptions of much of the apparatus once described in relation to a FIGURE is not repeated in the descriptions of subsequent FIGURES, although such apparatus or process is labeled with the same reference numbers.

The thyroid gland regulates hormones that controls body metabolism. The hormones from the thyroid regulate a number of critical body functions, including respiration rate; heart rate, body weight, muscle strength, nervous systems, menstrual cycles, body temperature, and cholesterol levels. The thyroid gland, as part of the endocrine system, is involved in the production, storage, and release of hormones into circulatory system so that the hormones can interact with the body's cells. In a major function, the thyroid gland uses iodine from dietary sources to make two main hormones known as T3 (triiodothyronine) and T4 (thyroxine).

Proper levels of the T3 and T4 hormones are important in proper thyroid function. The production of the T3 and T4 hormones are controlled by the hypothalamus and pituitary glands which help maintain proper levels and balance of the T3 and T4 hormones and as further seen in reference to FIG. 1.

For many patients with a thyroid disorder, it can take months or years to obtain a proper diagnosis and subsequent regulation of the T3 and T4 levels. One side effect of improper T3 and T4 levels involve the body's inability to absorb needed vitamins and nutrients in an efficient manner. As such, additional secondary effects from the nutritional deficit can contribute to the numerous other symptoms that may arise from improper T3 and T4 hormone levels.

In accordance with the present invention, it has been found that a novel combination of vitamin and mineral supplements with proprietary chelating agents has been found to significantly improve the body's availability and uptake of vitamins and nutrients. This ability helps restore nutritional health and helps establish an improved base line condition for patients who are undergoing treatment for improper T3 and T4 hormone levels or an imbalance of T3 and T4 hormones.

While not wanting to be unduly limited by theory, upon information and belief the, proprietary chelating manual agents identified herein help provide a more efficient uptake of vitamins and nutrients within a patients body. Accordingly, a dose of vitamins and nutrients with the amino acid chelating agent allows for a greater bio-availability and absorption of the nutritional supplements as opposed to the nutritional supplements minus the chelating agents. Further, it has been found that not all chelating agents will provide the benefits noted in the formulation described herein. It is believed that significant improvements in uptake and synergistic results are attributable to the source of minerals which chelating agents (Albion®) as identified herein.

As seen in reference to FIG. 1, there is schematic diagram illustrating the pathway and cycle of the thyroid with respect to T3 and T4 hormone levels. The formulation set forth below has been found useful in helping the body maintain a healthy environment for the thyroid as well as improved nutritional health by more efficient uptake of minerals and nutrients taken in combination with the proprietary chelating agents.

As identified below, there are a number of vitamins and nutrients within the formulation that are important in thyroid health. Formulations and compositions for therapeutic and dietary supplements are well known in the art. One having ordinary skill in the art would be able to provide the composition set forth below in a suitable form for ingestion by an individual. Suitable formulations for vitamins and dietary supplements can also be seen in reference to U.S. Pat. No. 7,998,500, assigned to SDK VC Parma Holding Corporation and U.S. Pat. No. 5,879,698 assigned to Wyeth Corporation, the two patents being incorporated herein by reference in their entirety.

Table 1

Formula (One Adult Dosage)
Vitamin A (beta carotene) 2500-3500 IU
Vitamin C (Ascorbic Acid) 250-700 mg
Vitamin D3 (Cholecalciferol) 3000-6000 IU
Vitamin E (d-alpha tocopherol) 15-30 IU
Vitamin K (phytonadione) 10-50 mcg
Vitamin B1 (thiamin HCl) 0.75-3.0 mg
Vitamin B2 (riboflavin) 1.0-2.5 mg
Niacin 10-40 mg
Vitamin B6 (pyridoxine HCl) 1-4 mg
Folic Acid 150-500 mcg
Vitamin B12 (methylcobalamin) 4-8 mcg
Biotin 250-1000 mcg
Pantothenic acid (Ca d-pantothenate) 2.5-20 mg
Calcium (Ca Carbonate) 200-1500 mg
Iron (ferrous fumarate) 10-30 mg
Iodine 75-300 mcg
Zinc (Zn Oxide) 7.5-35 mg
Magnesium (as Mg Citrate) 100-300 mg
*Selenium (Se AAC) 7.5-30 mcg
*Copper (Cu AAC) 0.5-4.0 mg
*Manganese (Mn AAC) 0.5-4.0 mg
*Chromium (Chromium Nictonate Glycinate) 80-200 mcg
(*Albion® (Clearfield, Utah USA) brand amino acid chelated minerals are used as indicated above)

The formula identified above provides one adult dosage in the form of a daily supplement. When one of ordinary skill in the art would realize that the adult dosage could be provided in a single tablet or capsule or be available in a less concentrated form that would involve multiple tablets or capsules being utilized to provide a recommended adult dosage. The nutritional supplement described herein can be made in a variety of forms, such as the following pharmaceutical compositions; a pill, a tablet, a caplet, a capsule, a chewable tablet, a quick dissolved tablet, an effervescent tablet, a hard gelatin capsule, a soft gelatin capsule, a powder, a liquid suspension, and a food product. One skilled in the art would recognize that there are also other viable ways for delivering the nutritional supplement to a user.

The following nutrients play critical roles in helping maintain healthy thyroid function: iodine, vitamin A, vitamin B-12, magnesium, zinc, selenium, thiamine copper, vitamin D, iron, riboflavin, manganese and vitamin C.

Iodine—Iodine is an essential component of Thyroxine (T4), which contains 4 molecules of iodine. The active form of Thyroid hormone, T3, contains 3 molecules of iodine. A deficit in iodine intake will result in hypothyroidism.

Vitamin A—Carotene is converted into vitamin A. However, an individual who is hypothyroid cannot efficiently convert beta carotene into vitamin A. It has been shown that people who are low in actual vitamin A have their ability to produce TSH is limited. Vitamin A also helps to convert T4 to T3. It should be noted that vitamin A requires protein to help in its absorption.

Vitamin B-12—Hypothyroidism can compromise one's ability to absorb vitamin B-12. It has been reported that 4.6% of the US population aged 12 and above suffer from hypothyroidism. In addition, another study found that 40% of hypothyroid patients suffer from vitamin B-12 deficiency. Adding vitamin B-12 supplementation to hypothyroid patients improved several symptoms of hypothyroidism including improvements to strength, memory, mood, and other symptoms.

Magnesium—The incidence of marginal magnesium deficiency is seen in 70% of the US population. Magnesium deficiency is commonly found in Hashimoto's Thyroiditis. Magnesium is a vital mineral for the functioning of the thyroid. It is one of the nutrients involved in the formation of TSH (thyroid stimulating hormone), which is produced and released into the blood stream by the pituitary gland. In addition, magnesium is also involved in the conversion of thyroxine (T4, the less active thyroid hormone) into the highly active form of the thyroid hormone, T3 is roughly 4 times as active as T4.

Zinc—Zinc is one of the most versatile nutrients relative to thyroid function. Zinc deficiency has been shown to have negative impacts on the hypothalamic-pituitary-thyroid function. Zinc is needed to stimulate the hypothalamus' thyroid hormone receptors. Without enough zinc, the hypothalamus can't properly gauge the thyroid hormone levels to increase production when thyroid levels are low. Zinc is essential to maintaining healthy levels of triiodothyronine (T3). Zinc plays a positive role in thyroid hormone metabolism. It helps maintain proper serum levels of T3, T4, and TSH.

Selenium—In adults, the thyroid gland contains the highest amount of selenium per gram of tissue. It is a critical component of the enzyme system (iodothyronine deiodinases) that removes an iodine atom from the external ring of T4, converting it into the more active T3 form of thyroid hormone. Selenium also plays a role in protecting the thyroid gland. In the process of making thyroid hormones, the thyroid gland generates hydrogen peroxide. Selenium is a component of glutathione peroxidase, which is the intracellular antioxidant defense against the free radical damage that can be caused by hydrogen peroxide. If there is inadequate selenium, high iodine levels may cause the destruction of thyroid gland cells.

Thiamine (Vitamin B-1)—Thyroid disease and autoimmune thyroid conditions (Hashimoto's Thyroiditis) have been seen to be associated with thiamine insufficiency. This can occur even after an individual has been receiving supplemental thyroid medication. Protein breakdown is accelerated in hypothyroidism. When protein is catabolized, this can result in elevated ammonia levels. Excess ammonia levels can have a negative impact on mental clarity, which is one of the main causes of the "brain fog" commonly seen in hypothyroidism. Thiamine helps this condition by preventing protein catabolism. As a result, supplemental thiamine can lead to improvement in brain fog, mental clarity, and memory recall. Other benefits of thiamine include improved metabolism, increased energy, improved blood sugar regulation, and protection from estrogen dominance Copper—Copper is important to normal brain development and that its deficiency renders the hypothalamus incapable of regulating thyroid hormone properly. In animal studies, copper deficient animals gave birth to infants that produced 48% less T3 than those in healthy mothers. In addition, copper is involved in the formation of tyrosine, which is the amino acid backbone of thyroid hormone T4.

Vitamin D—Vitamin D is recognized as an immune modulator. Vitamin D plays a significant role in reducing the incidence of autoimmune disease. Hashimoto's Thyroiditis is an autoimmune disease in which antibodies are formed against the thyroid gland, resulting in a form hypothyroidism. Often, patients with hypothyroidism suffer from hypovitamnoasis D with hypocalcemia, and that the degree of deficiency is significantly associated with the degree and severity of hypothyroidism.

Iron—Low iron is often seen in the hypothyroid patient. Hypothyroidism can lead to low iron, and low iron can worsen hypothyroidism. Hypothyroidism can cause a decrease in the production of stomach acid, which can lead to a decrease in the absorption of vital nutrients. Iron is a mineral that requires stomach acid for its absorption. In addition, iron is a component of many of the digestive enzymes. So low iron has multiple impacts on the hypothyroid patient. Iron is a component of the enzyme thyroid peroxidase, which catalyzes the first two steps in thyroid hormone production. The conversion of T4 to T3 results from deiodinase activity, which also requires the stimulus of thyroid peroxidase. Low iron will slow down thyroid activity through a decrease in thyroid hormone production and a lower rate of conversion of T4 to T3.

Riboflavin (Vitamin B-2)—This vitamin assists iodine in the formation of thyroxine (T4). In addition, the thyroid gland called contains a symporter. The symporter allows the entry of iodine into the thyroid gland. Riboflavin is required for the symporter to function properly.

Manganese—This mineral is essential to the formation of thyroxine, and manganese deficiency can contribute to hypothyroidism.

Vitamin C—Patients with hypothyroidism have been demonstrated to have a high degree of oxidative stress. In this case, vitamin C helps the hypothyroid patient through its action as an antioxidant. It has been seen that some patients poorly absorb levothyroxine. Studies have shown that taking levothyroxine with vitamin C will increase the absorption of the levothyroxine. Vitamin C has also been shown to play a role in the formation of thyroxine.

Celiac disease often co-occurs with other autoimmune disorders, like Hashimoto's Thyroiditis (which accounts for 90-95% of all cases of hypothyroidism). People with celiac disease have gluten intolerance. Recent research is suggesting that everyone with an autoimmune condition has gluten sensitivity that is not always celiac mediated. People with Hashimoto's Thyroiditis often are gluten intolerant. People with this autoimmune disorder, when eating gluten, will have their body attack the lining of their small intestine. These attacks destroy the intestinal villi that help to digest and absorb nutrients. Damage to the villi leads to a person becoming malnourished, because they are not able to absorb the nutrients in the food they consume. Additionally, certain minerals are more difficult to absorb than others.

The use of amino acid chelated minerals and complex minerals as identified above and as obtained from Albion® have been found to offer improved bio-availability of the overall formulation provided herein in comparison to other versions of chelated minerals. Accordingly, in the formulation described above, the use of the Albion® chelates has been found to offer superior performance as opposed to using other materials sourced by different manufacturers.

The roles of certain vitamins and minerals, along with the amino acid tyrosine, make their intake very important in the support of an individual with hypothyroidism. The use of medications, like thyroid hormone or levothyroxine sodium may appear to work initially, but they do not lead to long term improvement of the patient's thyroid issues, because they do not address the underlying cause: nutrient deficiency. The negative impact of these nutrient deficiencies can lead to overmedication of the patient with low levels of TSH, which can lead to symptoms of hyperthyroidism: rapid heart rate, night sweats, anxiety, hot flashes, and insomnia.

The formulation described and claimed herein has been found useful for treating thyroid conditions associated with an imbalance of proper T3 and T4 ratios as well as thyroid influenced hormone levels that may be excessively high or low. In addition, the increased bio-availability of the formulation described herein is also useful for individuals suffering from auto-immune diseases that often affect the body's ability to absorb nutrients from a traditional diet. The combination of vitamins and nutrients described above has been found to enhance the bio-availability of the vitamins and minerals. The resulting increase in nutritional health can help a patient in a number of improved responses that are related to thyroid health, nutritional deficiencies, and intestinal and digestive disorders that frequently impair the body's ability to efficiently absorb vitamins and nutrients from dietary sources.

The formulation described above can also be used as a form of treating a medical condition related to restoring thyroid and health and function based on hormonal imbalances. As such, the present invention includes a method of treating a thyroid hormone imbalance comprising the steps of:

administering to a patient a nutritional supplement comprising:
Vitamin A (beta carotene) in about 2500-3500 IU;
Vitamin C (Ascorbic Acid) in about 250-700 mg;
Vitamin D3 (Cholecalciferol) In about 3000-6000 IU;
Vitamin E (d-alpha tocopherol) in about 15-30 IU;
Vitamin K (phytonadione) in about 10-50 mcg;
Vitamin B1 (thiamin HCl) in about 0.75-3.0 mg;
Vitamin B2 (riboflavin) in about 1.0-2.5 mg;
Niacin in about 10-40 mg;
Vitamin B6 (pyridoxine HCl) in about 1-4 mg;
Folic Acid in about 150-500 mcg;
Vitamin B12 in about (methylcobalamin) 4-8 mcg;
Biotin in about 250-1000 mcg;
Pantothenic acid (Ca d-pantothenate) in about 2.5-20 mg;
Calcium (Ca Carbonate) in about 200-1500 mg;
Iron (ferrous fumarate) in about 10-30 mg;
Iodine in about 75-300 mcg;
Zinc (Zn Oxide) in about 7.5-35 mg;
Magnesium (as Mg Citrate) in about 100-300 mg;
Selenium (Se AAC) in about 7.5-30 mcg;
Copper (Cu AAC) In about 0.5-4.0 mg;
Manganese (Mn AAC) in about 0.5-4.0 mg; and,
Chromium (Chromium Nictonate Glycinate) in about 80-200 mcg
wherein the nutritional supplement is continued until target levels of T3 and T4 hormones are restored.

The present invention also includes a nutritional supplement as described herein in which the nutritional supplement treats hormone related thyroid disorders, auto-immune disorders, and digestive disorders. Specifically, the formulation of above formulation and the method of using it allows one to improve blood sugar levels, A1C levels and triglycerides levels in diabetic patients.

Further, it has been found that the formulation helps reduce symptoms of patients suffering from fibromyalgia. Similar improvements in the control of chronic conditions such as colonitis have been achieved as well. The formulation and process of using the formulation is also helpful in restoring proper balance, ratios, and levels of T3 and T4 hormones. In addition, patients who have had a thyroidectomy or radiation treatments, which impair the normal thyroid function, the above formulation and process of using the formulation reduces symptoms associated with a less active thyroid and, described above, improved the T3 and T4 ratios and hormone levels.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

That which is claimed:

1. A nutritional supplement in the form of a tablet or capsule consisting of:
Vitamin A in about 2500-3500 IU;
Vitamin C in about 250-700 mg;
Vitamin D3 in about 3000-6000 IU;
Vitamin E in about 15-30 IU;
Vitamin K in about 10-50 mcg;
Vitamin B1 in about 0.75-3.0 mg;
Vitamin B2 in about 1.0-2.5 mg;
Niacin in about 10-40 mg;
Vitamin B6 in about 1-4 mg;
Folic Acid in about 150-500 mcg;
Vitamin B12 in about 4-8 mcg;
Biotin in about 250-1000 mcg;
Pantothenic acid in about 2.5-20 mg;
Calcium in about 200-1500 mg;
Iron in about 10-30 mg;
Iodine in about 75-300 mcg;
Zinc Oxide in about 7.5-35 mg;
Magnesium in about 100-300 mg;
Selenium in about 7.5-30 mcg;
Copper in about 0.5-4.0 mg;
Manganese in about 0.5-4.0 mg; and,
Chromium in about 80-200 mcg.

2. A dosing formulation for a composition, the dosing formulation comprising a single dosage formulation of the composition, wherein the composition consist of:
Vitamin A 2500 IU;
Vitamin C 500 mg;
Vitamin D3 4000 IU;
Vitamin E 22.5 IU;
Vitamin K 25 mcg;
Vitamin B1 1.5 mg;
Vitamin B2 1.7 mg;
Niacin 20 mg;
Vitamin B6 2 mg;
Folic Acid 400 mcg;
Vitamin B12 6 mcg;
Biotin 500 mcg;
Pantothenic acid 10 mg;
Calcium 600 mg;
Iron 18 mg;
Iodine 150 mcg;
Zinc 15 mg;
Selenium 20 mcg;
Copper 2 mg;
Manganese 2 mg;
Chromium 120 mcg; and,
Magnesium (Mg Citrate) 200 mg.

3. The nutritional supplement according to claim 1 wherein the Selenium, Copper, Manganese, and Chromium are in the form of chelated minerals.

4. The formulation according to claim 2 wherein the Selenium, Copper, Manganese, and Chromium are in the form of chelated minerals.

* * * * *